United States Patent [19]

Paciorek et al.

[11] Patent Number: 4,906,763

[45] Date of Patent: * Mar. 6, 1990

[54] BORON NITRIDE PRECERAMIC POLYMERS

[76] Inventors: Kazimiera J. L. Paciorek, 1425 Seacrest Dr., Corona Del Mar, Calif. 92625; Reinhold H. Kratzer, 17 Shooting Star, Irvine, Calif. 92714; David H. Harris, 201 N. Lima St., Sierra Madre, Calif. 91024; Wilfried Krone-Schmidt, 11637 Cullman Ave., Whittier, Calif. 90604

[ * ] Notice: The portion of the term of this patent subsequent to Nov. 17, 2004 has been disclaimed.

[21] Appl. No.: 120,335

[22] Filed: Nov. 13, 1987

Related U.S. Application Data

[63] Continuation-in-part of Ser. No. 14,700, Feb. 13, 1987, Pat. No. 4,707,556.

[51] Int. Cl.$^4$ .......................... C07F 5/05; C07F 7/10; C07F 7/21
[52] U.S. Cl. .................................. 556/403; 528/12; 528/30
[58] Field of Search ...................... 556/403; 528/30, 12

[56] References Cited

U.S. PATENT DOCUMENTS 3,382,279  5/1968  Horn et al. ................. 556/403
4,581,468  4/1986  Paciorek et al. ............ 556/403
4,707,556  11/1987  Paciorek et al. ............ 556/403

OTHER PUBLICATIONS

Paciorek et al., "Boron-Nitrogen Polymers, I, Mechanistic Studies of Borazine Pyrolysis".
Paciorek et al., "Study of Borazine Condensation Process".

*Primary Examiner*—Paul F. Shaver
*Attorney, Agent, or Firm*—Knobbe, Martens, Olson & Bear

[57] ABSTRACT

A preceramic substituted borazine polymer of the formula:

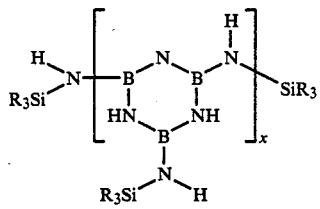

wherein R is methyl, ethyl, propyl, or butyl, and x is a positive integer. Also disclosed are methods for making the polymer, methods for converting the polymer into coatings, shaped articles, articles including fibers and filaments formed from the polymer, blends of the foregoing polymer and preceramic triamino-N-tris (trialkylsilyl) borazines, and methods for thermally decomposing the foregoing polymers to form shaped articles of boron nitride.

11 Claims, No Drawings

BORON NITRIDE PRECERAMIC POLYMERS

RIGHTS OF THE GOVERNMENT

This invention was made in part with government support under Contract N00014-85-C-0659 awarded by the Department of the Navy. The government has certain rights in this invention.

CROSS-REFERENCE TO RELATED APPLICATION

This application is a continuation-in-part of U.S. Ser. No. 014,700 filed Feb. 13, 1987, now U.S. Pat. No. 4,707,556.

BACKGROUND OF THE INVENTION

This invention relates to the synthesis of substituted borazines, the thermal polymerization of these borazines, and the final transformation of the preceramic borazine polymers into carbon-free boron nitride ceramic.

Ceramic materials, of which boron nitride is representative, have unique properties of great commercial importance. However, due to their insolubility and nonfusibility, the processing of these materials into useful end-products presents serious difficulties. Bulk boron nitride is commonly prepared by fusion of borax with ammonium chloride (Tied, H. et al., Z. Anorg. Allgem. Chem. 147, p. 114 (1925)) or fusion of boric anhydride with urea in an ammonia atmosphere (O'Connor, T., J. Am. Chem. Soc. 84, p. 1753 (1952)). However, because of its nonfusible and insoluble ceramic nature, the bulk material is not useful in applying boron nitride as a coating to complex surfaces or forming it into complex shapes. For these purposes, it is necessary to generate boron nitride in situ from soluble, processible precursors. A critical requirement for such precursors is that the boron nitride they yield on fusion should be free of carbon, a troublesome impurity in ceramics.

Borazines are potentially suitable as this type of boron nitride precursor because of their ability to form soluble polymers on heating. Preceramic polymers based on borazines where no carbon is bonded to either boron or nitrogen are most suitable for the production of pure boron nitride fibers and coatings.

The literature reports the polymerization of a few substituted borazines; but the mechanism of reaction as well as the chemical structure and composition of the polymers is not clear, so it is not always possible to predict the structure or composition of the product of a synthesis. Gerrard, W. et al., J. Chem. Soc., p. 113 (1962), postulated that the interaction of chloroborazine with a class of molecules represented by di-s-butylamine would produce polymerized borazine rings attached through ring boron and nitrogen atoms; however, the polymerization of B-tris (ethylamino)-N-triethyl borazine on heating for four hours at 300° C. was reported to polymerize to borazine rings joined by ethyl-substituted nitrogen atoms.

A method to produce polymers of borazines consisting of a repeated structure of boron-nitrogen bonds and using various alkyl aminoborazines as starting material is the subject of a Japanese patent (Japanese Patent No. 37,837 (1978) to Tanaguchi). However, a careful reproduction of this procedure was found to produce polymers whose pyrolysates were impure boron nitride due to carbon retention (Paciorek, K. et al., J. of Polymer Sci. 24, pp. 173–185 (1986)).

The inventors have produced borazine polymer capable of final transformation into carbon-free boron nitride by the synthesis of triamino-N-tris (trialkylsilyl) borazines and subsequent thermal condensation into preceramic polymer. The composition and method are the subject of U.S. Pat. No. 4,581,468 (1986). This polymer is referred to herein as polymer A.

It is the principal object of the present invention to provide a preceramic borazine polymer having a different structure from the previous patented material, but which is also capable of undergoing a conversion to pure boron nitride upon pyrolysis. The polymer of the present invention is referred to herein as polymer B.

The organic solvent-soluble polymers A and B can be used as precursors to permit the use of boron nitride ceramic in applications otherwise impractical or impossible. After the preceramic polymer is appropriately placed, it can be transformed under reactive conditions, which remove substituent groups from the polymerized borazine rings, into a residue of pure boron nitride.

A readily processible polymer which upon pyrolysis can be so transformed into a pure boron nitride ceramic offers a potential for producing the ceramic in many useful physical forms, including fibers, shaped articles, coatings, foams, and also as a binder for ceramic powders which would eliminate the use of additives (i.e., sintering aids).

It is another principal object of this invention, therefore, to provide a suitable preceramic polymer which is soluble in organic solvents, and which can be formed into solvent spun fibers or coatings.

It is also an object of this invention to provide processes for transforming the preceramic polymer into fibers, coatings and shaped articles of pure boron nitride ceramic.

Other objects and advantages of the invention will become apparent to those skilled in the art upon consideration of the accompanying disclosure.

SUMMARY OF THE INVENTION

The present invention resides in the synthesis of the preceramic polymer of the general formula:

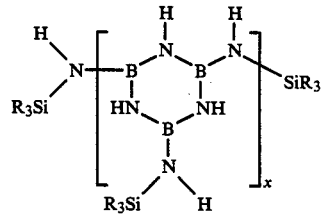

wherein R is methyl, ethyl, propyl, or butyl, and x is a positive integer.

In accordance with an object of the invention there is hereby provided a new preceramic substituted borazine polymer having a structure and properties distinct from that previously disclosed, but also capable of undergoing thermal transformation into pure boron nitride ceramic.

There is provided also a method of synthesizing this borazine polymer by reacting chloroborazine with a disilazane, both reactants being dissolved in a mixture of organic solvents having at least one aromatic component and at least one non-polar aliphatic component, while carrying out the reaction in the presence of a non-reactive gas. The reactants are allowed to interact at a low temperature between −78° and 0° C. for between 4 to 24 hours, after which time the temperature is allowed to come to ambient temperature and the precipitated by-products are removed by filtration. The soluble polymer product is isolated by removing the solvent from the filtrate.

In a preferred embodiment, the reaction is carried out in an atmosphere of nitrogen, argon, or helium, or a mixture of those gases, at or about atmospheric pressure. In a particularly preferred embodiment, the synthesis is carried out in an equal mixture of benzene and hexane in a nitrogen atmosphere for a period of from about 3 to 24 hours at temperatures from about 0°–50° to −30° C.

In accordance with another object of the invention there is provided a process of preparing boron nitride ceramic from a substituted borazine polymer precursor, in which the borazine polymer precursor is heated in an atmosphere of ammonia gas at a rate required to bring the temperature to about 1000° C. within a period of 4 to 30 hours. The system is allowed to cool to an intermediate temperature between 300° and 400° C. The ammonia gas is evacuated from the system while allowing the system to cool to ambient temperature and nitrogen or another non-reactive gas is then supplied to bring the system to atmospheric pressure. In a preferred embodiment, the ammonia atmosphere in the system is at a pressure from between 400 to 760 mm Hg.

There is also provided an analogous process of preparing boron nitride ceramic from a substituted borazine polymer precursor wherein the substituted borazine polymer precursor is heated in an atmosphere of halide acid gas at a temperature of from about 50° C. to 60° C. for a period of from about 10 to 20 hours preliminary to the treatment with ammonia gas. The use of this procedure reduces the period of treatment with ammonia gas required to transform polymer A to boron nitride ceramic about 10-fold. In a particularly preferred embodiment of this process, the halide gas is hydrogen chloride (HCl) present at a pressure of approximately 100 mm Hg. and the ammonia gas is present at a pressure of approximately 500 mm Hg.

In preferred embodiments of both curing processes, the borazine rings in the borazine polymers are substituted with silylamino groups. In a particularly preferred embodiment of the procedure using a halide acid gas, the borazine polymers have the structure of polymer A.

We have now found that it is possible to make fibers and shaped and coated articles from polymers of A and B. Accordingly in yet another embodiment of the invention, there are provided substituted borazine polymers in the form of fibers prepared by melt-drawing a system of at least one substituted borazine polymer at a temperature below that at which polymer is converted to boron nitride. In a preferred embodiment, the fibers are melt-drawn from polymer A and in another preferred embodiment the fibers are melt-drawn from polymers A and B. In a particularly preferred embodiment, the boron nitride ceramic fibers are produced from a system of substituted borazine polymers A and B present in equal proportions.

In accordance with yet another embodiment of the invention, there are provided borazine polymers in the form of shaped articles prepared by processes of casting or extruding fusible polymers or evaporating polymer solutions.

In accordance with yet another embodiment of the invention, there is presented a process of coating an object with boron nitride comprising the steps of heating the object within a system to a temperature of about 1000° C., cooling it to ambient temperature, immersing it in a solution of a substituted borazine polymer so as to apply a polymer coating, and curing the polymer coating by heating at a temperature sufficient to convert preceramic polymer to boron nitride in the presence of ammonia gas.

In a particularly preferred embodiment of this process, the substituted borazine polymer is dissolved in a nonpolar organic solvent, such as hexane. Ammonia gas is present in the final thermal transformation at a pressure of 500 mm Hg.

There is further provided an analogous process of coating an object with pure boron nitride comprising a preliminary step of heating the polymer coated object in an atmosphere of hydrogen halide gas, after removing the object from the polymer solution and prior to proceeding to the thermal transformation step.

In particularly preferred embodiments of this process, the acid halide gas is HCl at a pressure of about 100 mm Hg.

In a preferred embodiment of the coating processes, the substituted borazine polymer has the general structure of polymer A.

DETAILED DESCRIPTION OF THE INVENTION

The substituted borazine polymers of this invention are of the general formula

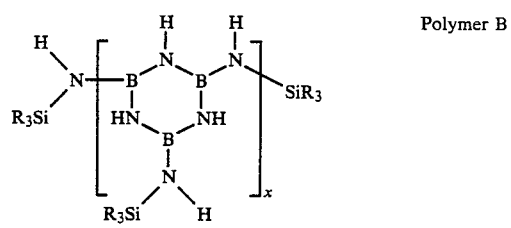

Polymer B wherein R is a lower alkyl group such as methyl, ethyl, propyl or butyl having the formula $C_nH_{2n+1}$ and x is a positive integer.

Polymer B is conveniently synthesized by the reaction of chloroborazine (a compound described by Laubengayer, A., et al. (1955) *J. Amer. Chem. Soc.* 77, pp. 3699–3700) with a disilazane.

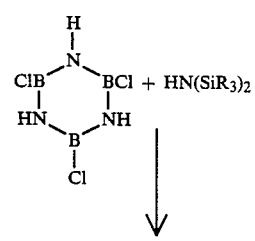

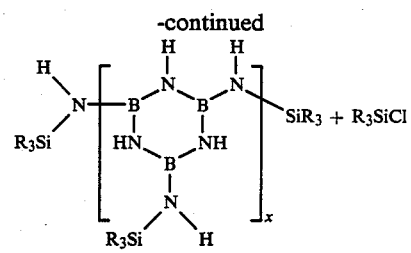
+ R$_3$SiCl

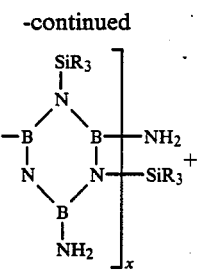
+

The synthetic reaction between chloroborazine and disilazane is preferably carried out over a period of 4 to 2 hours in the cold (e.g., at temperatures between −78° and 0° C.), in a mixed aliphatic/aromatic solvent system, in the atmosphere of a non-reactive gas. The procedure is described in detail in Example I.

The synthesis procedure consists of introducing a solution of chloroborazine dissolved in a mixed aliphatic/aromatic solvent system into a disilazane, dissolved in an aliphatic solvent. During the reaction process a precipitate forms which is composed of a high molecular weight polymer. At the end of the reaction, this precipitate is filtered off and the desired product, a soluble silylamino-substituted borazine polymer, is isolated by evaporating the solvent from the filtrate.

The use of an aromatic solvent is utilized to introduce chloroborazine into the reaction. This solvent may be toluene or xylene but is preferably benzene, either alone or mixed with a saturated aliphatic solvent. The disilazane is introduced in an aliphatic solvent of the same type, such as heptane or preferably hexane.

Using the same substituted disilazane as a reactant, the choice of solvents and the temperature at which the reaction is carried out are important determinants of the yield of soluble polymer and its average molecular weight.

The product polymers comprise a range of oligomers. Different solvent systems yield polymers of different molecular weight distributions. Given a single solvent system, the upper limit of the molecular weight of the useful product polymer is the solubility of polymer in that system. If the molecular weight of a polymer exceeds the limit of solubility, that polymer will precipitate out and be irreversibly insoluble.

Temperature influences the yield of soluble polymer. At the limit (room temperature), it has been found that all polymer produced is insoluble and infusible.

The synthesis and properties of Polymer B are compared with those of Polymer A (disclosed in our U.S. Pat. No. 4,581,468), of the following general formula, where X is a positive number, such as 1, 2, 3, or 4, and R is lower alkyl, such as methyl, ethyl, propyl, or butyl:

Polymer A

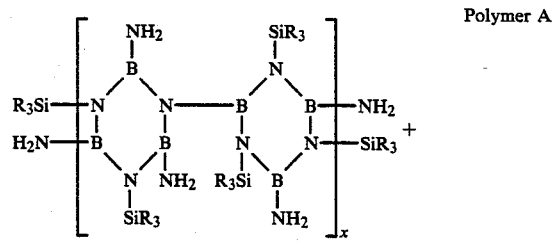

Polymer A is conveniently synthesized by the reaction of ammonia gas with B-trichloro-N-tris (trialkylsilyl) borazine, described by Geymayer, P., et al. (1964), *Anoewandte Chemie Internat. Edit.* 3, p. 633. Replacement of chloride groups by amino groups yields a monomer readily condensable into doubly and singly bridged dimers, further condensable into polymeric form.

This reaction is usually conducted at temperatures ranging from −78° to 25° C. The reaction period ranges from 4 to 24 hours, although longer or shorter periods can be used. The reaction is carried out under a non-reacting gas such as nitrogen, helium, or argon. In general, ammonia is used in 2- to 10-fold excess over what is required by the stoichiometry of the reaction. Subsequent condensation to the preceramic polymer is accomplished at temperatures ranging from 50° to 300° C. over a period of 8 to 250 hours, either in a nonreactive gas such as nitrogen, helium, or argon, or in vacuo.

The present invention also includes boron nitride fabrications comprising fibers, coatings and shaped articles which can be prepared from polymers A and B and their mixtures.

Boron nitride coatings may be applied to articles by dipping the article in liquified borazine polymer, and then curing the polymer coating to boron nitride, as described in Example V.

Borazine polymers may be spun or drawn into fibers by a variety of processes well known to those skilled in the art (see J. Riley, Chapter XVIII: Spinning and Drawing Fibers, in Polymer Processes, C. Schildknecht (Ed.), Interscience, New York, 1956). To obtain final boron nitride articles such as fibers, the preceramic fibers are drawn from a melt of the condensed polymer A. The preceramic fibers are then transformed to boron nitride fibers by heating in gaseous ammonia at temperatures increased gradually from 60° to 1000° C. over time periods ranging from 8 hours to 27 days. The polymer is also amenable to solution fiber spinning.

Preparation of B-triamino-N-tris (Trimethylsilyl) Borazine and Condensation Products thereof Under nitrogen bypass to liquid ammonia (20 ml) in a three-neck 100 ml flask equipped with a dry ice condenser and addition funnel, was added B-trichloro-N-tris (trimethylsilyl) borazine (10.0 g, 24.98 mmol) in hexane (50 ml) over a period of 1.6 hours. The addition was accompanied by the formation of a white precipitate. Subsequently, the mixture was allowed to warm slowly to room temperature. Filtration in the non-reacting atmosphere gave 4.04 g (100% yield) of ammonium chloride. The filtrate, after removal of the solvent, gave the crude B-triamino-N-tris (trimethylsilyl) borazine (7.38 g, 86% yield). A 6.60 g portion was subjected to in vacuo distillation at 135° C. which resulted in the removal of a by-product, boiling in the ranges of 75° to 87° C. (1.05 g, 15.9% yield). The semi-liquid residue (4.80 g) consisted of a 2:1 mixture of the doubly-bridged borazine dimers and tetramers.

Elemental Analysis:

Calculated for: $C_{14}H_{51.33}N_{12.67}B_8Si_{4.67}$: B, 14.06%; N, 28.86%; MW, 615. Found for product: B, 13.46%; N, 26.76%; MW, 620.

To achieve further condensation to preceramic polymer, the above mixture of dimers and tetramers was subjected to heat treatments at 196° to 260° C.

The preceramic polymer consisted of a mixture of doubly-bridged tetramers and octamers.

Elemental Analysis:

Calculated for: $C_{22}H_{80.67}N_{23.33}B_{16}Si_{7.33}$: B, 16.46%; N, 31.09%; MW, 1051. Found for product: B, 16.01%; N, 29.39%; MW, 1010.

Boron nitride ceramic that is contaminated with carbon is unsuitable for many applications. Both Polymers A and B are capable of being transformed to substantially pure boron nitride ceramic because the substituents on the borazine side chains constitute leaving groups which remove carbon efficiently under the conditions of high temperature and in the presence of ammonia gas which exist when the borazine rings of the polymers undergo a final condensation during the curing process. Ammonia is essential to the elimination of carbon in this process.

The elimination of carbon from Polymer B is demonstrated in the thermal transformation of bulk polymer to bulk boron nitride in Example II.

Polymer A and B differ markedly in the physical characteristic of fusibility, the tendency to melt and coalesce. Polymer B, as synthesized, is relatively infusible; polymer A, on the other hand, as synthesized, has a low melting point, approximately 90° C.

The melting point of polymer A can be increased by gradual heating to further condense the oligomers, thereby increasing the molecular weight. In this condensation process, the temperature is raised gradually. This is usually from about 50° C. to about 300° C. over a period of from 8 hours to 10 days in an atmosphere of non-reacting gas.

After this treatment, polymer A may be melt drawn into fibers, spun, or otherwise processed at a temperature of about 120° C. to 160° C. Subsequent curing and transformation of the processed polymer A to boron nitride requires a further, preferably gradual heating to about 1000° C. in an ammonia atmosphere, typically requiring, as in the case of the fibers, a period of 12 days. The curing of polymer A can be accelerated, however, by pretreating the processed polymer fibers with heat in the presence of a hydrogen halide such as HCl gas as described in Example IV. This pretreatment "hardens" the fiber so that it is infusible, preventing softening thereof during the curing process. The time necessary to transform these HCl-treated fibers to boron nitride by heating to 1000° C. under ammonia is consequently reduced from 12 days to 12 hours.

Polymers A and B either alone or in combination can be processed so that the boron nitride ceramic they yield on thermal transformation can be adapted to many specific applications.

One method of processing these preceramic polymers is by producing a polymer fiber. Preceramic polymer fibers were melt drawn at 90° to 160° C. from polymer A, and subsequently transformed into boron nitride ceramic fibers by gradual heating in an ammonia atmosphere from 60° to 1000° C. over a period of 12 days. Gradual heating is preferred in order to more fully polymerize polymer A as it heats so that it does not soften and melt during curing.

An improved fiber was produced by melt-drawing a mixture of polymers A and B as described in Example III. Both types of fiber were completely colorless, free of carbon and did not melt or lose weight when heated in nitrogen at 1000° C.

Combining polymers A and B to melt draw a fiber of mixed composition provides some advantages. Polymer B is cheaper and it shrinks less during transformation, hence it serves as an excellent extender. More important, however, is the fact that the presence of polymer B imparts a rigidity to the fibers in the early stages of transformation to boron nitride which permits the process to proceed at a rate about 10-fold faster than the same process using pure polymer A fibers.

Polymer fibers melt drawn from a mixture of polymers A and B do not require a condensation prior to fiber production or a pretreatment prior to the curing process. The mixed polymer fibers are converted to nitride by heating to about 1000° C. under ammonia for a period of only 25 hours.

It should be emphasized that the foregoing times and temperatures relate to bench scale processes. It is foreseen that the process can be greatly accelerated and that higher temperatures may be used in a production scale process.

A variety of other processes known in the art may also be suitable for processing borazine polymers into fibers. (See, e.g., J. Riley, Chap. XVIII: "Spinning and Drawing Fibers," in Polymer Processes, C. Schildknecht (Ed.), Interscience, New York, 1956).

In spinning processes, fiber-forming polymer, in a temporarily fluid state, is extruded under pressure from a multiplicity of orifices of a jet or spinneret, and assumes a solid state in the form of a fiber. Polymer may be either melted or dissolved in a suitable solvent to make it fluid. Suitable solvents for these polymers include hexane, heptane, benzene, toluene, xylene and other organic non-reactive solvents, including mixtures of solvents.

In melt-spinning, the melted polymer emerges from the spinneret in the dimensions of fiber or filament but still in a liquid state. Its solidification is sped up by a cool current of non-reactive gas. Filament so produced may be removed at constant speed by a drive wheel and then taken up by a spool or bobbin.

In solution spinning, polymer that is dissolved in a solvent is spun into fiber or filament in one of two ways, dry spinning or wet spinning. In dry spinning, the dissolved polymer is forced through the spinneret, emerging as a fine stream into a zone in which solvent is removed rapidly enough so that the fine streams become dimensionally stable, and do not adhere or contact. The solvent may be removed by allowing the stream to pass through a heated cabinet which has a circulating atmosphere of warm inert gas and in which the vapor pressure of solvent is kept low enough that the filament exterior is not redissolved by residual solvent. The process may be accelerated by diluting the original solvent with a less volatile non-solvent.

In wet solution spinning, the solvent is removed from the extruded streams of filament by passage through a liquid bath, known as a spin bath. The spin bath may be a non-solvent which diffuses rapidly into the filament to precipitate or coagulate it.

Melted polymer may also be spun by blasting the melt bath with a non-reactive gas, or shooting the melt through an inert gas at high speed, using drag forces to draw off streamers.

In all these processes, the borazine polymers are kept in an atmosphere of non-reactive gas, or stored under a non-reactive liquid, until the fibers are converted to boron nitride by curing as described in Example III. In any of the transformation processes for fibers, it is helpful to bring the temperature up to about 1200° C. at the end of the process while stretching the fibers.

Boron nitride may be fabricated as desired shapes by molding and casting borazine polymers preliminary to curing in several ways. (See, e.g., J. Manson, "Polymers," Vol. 10, pp. 634–35, McGraw-Hill Encyclopedia of Technology, 5th Ed. (1982)). It is believed that such standard techniques as compression molding, injection molding, extrusion, and casting can be adapted to use with the present polymers.

The characteristics of each of the polymers confers advantages in particular applications. The transformation of polymer A under the ammonia process described previously requires long gradual heating cycles to further polymerize and thereby raise the initial low softening point of the polymer, but a low softening point at the same time is desirable if fibers and filaments are to be drawn or spun from a melt. The non-fusible nature of polymer B makes it possible to cure and transform it to pure boron nitride in as little as 7 hours (Example II), and is also important in the process described for coating alumina fibers or other fibers (Example V). If polymer A alone were used for coating the fibers, its tendency to fuse and coalesce would produce a soft and sticky coating, and the fibers would clump and mat together.

Each of polymers A and B contributes its respective properties to fibers which can be drawn, without the need for a prior condensation, from a mixture of polymers A and B, fibers which cure, without preliminary HCl treatment, in 25 hours.

One of the more useful applications of boron nitride ceramics is to provide a protective coating on material so as to prevent chemical or physical change. A boron nitride coating can provide a barrier to prevent an undesired interaction (such as a chemical reaction or dissolution) between two otherwise incompatible materials; for example, a composite and the matrix in which it is embedded. It may also act as an electrical insulator or may provide a thermal barrier, allowing a material to perform a function at a temperature at which its integrity could not otherwise be maintained. The preceramic borazine polymers herein described are particularly well-suited to such coating applications. The object to be coated is immersed in a polymer solution, and then, through either of the processes described, the polymer is thermally transformed into a coating of pure boron nitride.

A specific application is in the coating of alumina fibers. Alumina fibers, when coated with boron nitride, can be used in glass, which would otherwise dissolve then. Example V provides a procedure for coating such fibers.

Because the coefficient of thermal expansion of boron nitride is low relative to many other materials, and because of the high thermal stability of the material, shaped articles of boron nitride may find particular utility in electronics applications, as components for internal combustion engines, and in other applications where these characteristics are important.

A more complete understanding of the invention can be obtained by referring to the following illustrative examples which are not intended, however, to unduly limit the invention.

EXAMPLE I

Preparation of Preceramic Polymer B

Under nitrogen by-pass to a stirred solution of hexamethyldisilazane (11.3 g, 70.0 mmol) in hexane (120 ml) was added at −50° to −40° C. a solution of chloroborazine (2.5 g, 13.6 mmol) in 1:1 benzene/hexane (25 ml) over a period of 1.5 hours. Following the addition, the solution was stirred at −35° C. for 1.5 hours; then the reaction mixture was allowed to warm up slowly to room temperature. The precipitate which formed, 0.6 g, was filtered off and on evaporation of the filtrate, 2.3 g of the preceramic polymer was obtained. The material was very soluble in hexane, more than 480 mg/660 mg hexane.

Elemental Analysis:

Calculated for: $C_{21}H_{89}N_{26}B_{17}Si_7$: C, 23.69; H, 8.42; N, 34.20; B, 15.23; Si, 18.45; MW, 1064.89. Found for product: C, 23.99; H, 8.20; N, 35.39; B, 14.88; MW, 1100.

EXAMPLE II

Bulk Boron Nitride Production

The preceramic polymer B, 102.5 mg, was heated from 25° to 990° C. over a period of 7 hours in a platinum cup inserted into a quartz tube under 500 mm Hg of ammonia. The white residue weighed 37.6 mg which corresponds to 63.32% weight loss.

Calculated weight loss for: $C_{21}H_{89}N_{26}B_{15}Si_7 \rightarrow 15$ BN is 65.04%.

The material was completely colorless, free of carbon and did not melt or lose any weight when heated in air at 1000° C.

EXAMPLE III

Boron Nitride Fiber Production

From a 1:1 mixture of polymers A and B, preceramic fibers were melt drawn. The fibers were transformed into boron nitride fibers by gradual heating in ammonia atmosphere from 68° to 970° C. over a period of 25 hours. The fibers thus produced were completely colorless, free of carbon, and did not melt or lose any weight when heated in air or nitrogen at 1000° C.

EXAMPLE IV

Boron Nitride Fiber Production: Preliminary HCl Treatment

Preceramic fibers melt drawn from polymer A were heated at 58° C. over a 16-hour period in a hydrogen chloride atmosphere at a pressure of 100 mm Hg. Thus treated fibers did not soften or melt up to 225° C. The fibers were then gradually heated in an ammonia atmosphere, 500 mm Hg, from 50° to 1000° C. over 12.5 hours. After cooling to 366° C. the system was evacuated, and once a temperature of 25° C. was reached, it was brought to atmospheric pressure with nitrogen.

EXAMPLE V

Boron Nitride Coated Alumina Fiber

A 200-filament section of a yarn of continuous polycrystalline alumina fibers (product of E. I. duPont de Nemours and Company) was heated gradually in a quartz tube from 25° to 620° C. in an air atmosphere over 3.5 hours to remove any surface coating. Subsequently, the system was evacuated and the temperature was raised to 985° C. over 3.25 hours. After the system cooled to room temperature, it was brought to atmospheric pressure by introducing nitrogen. The heat-treated fibers were then dipped into a hexane solution containing 9.6% by weight of the boron nitride preceramic polymer B contained in an inert atmosphere. The transformation of the preceramic polymer coating to pure boron nitride was accomplished by gradual heating from 100° to 977° C. over an 8-hour period in an ammonia atmosphere, 500 mm Hg. The system was cooled under vacuum to room temperature and brought to atmospheric pressure with nitrogen. The entire coating process was carried out twice. In this manner, alumina fibers coated by boron nitride ceramic were produced.

As will be evident to those skilled in the art, modifications of the present invention can be made in view of the foregoing disclosure without departing from the spirit and scope of the invention.

We claim:

1. The polymer

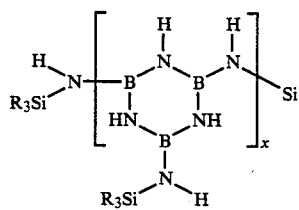

where R is methyl, ethyl, propyl or butyl of the general formula $C_nH_{2n+1}$ and where X is a positive integer, in the form of fibers or filaments.

2. The polymer

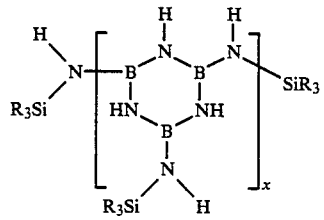

in the form of a shaped article.

3. A shaped article formed from one or both of the following polymers

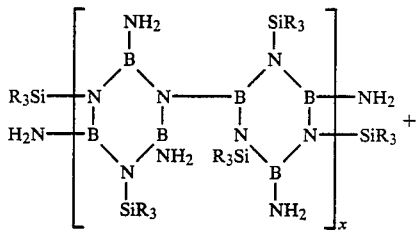

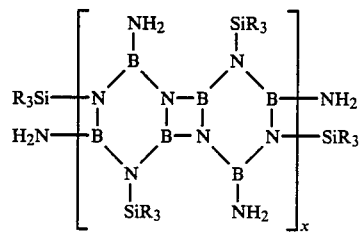

wherein R is lower alkyl of the general formula $C_nH_{2n+1}$, and X is a positive integer.

4. Fibers or filaments formed from a mixture of the polymer

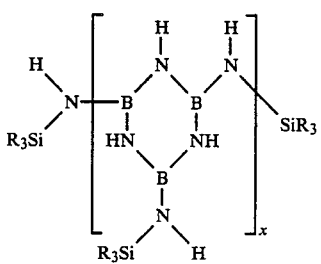

and one or both of the following polymers

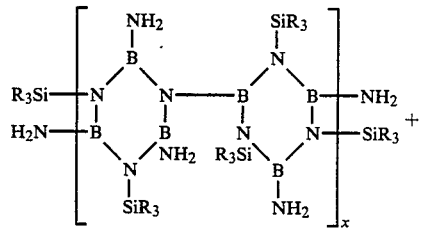

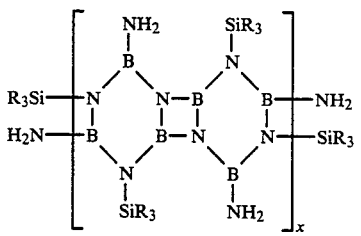

wherein R is lower alkyl of the general formula $C_nH_{2n+1}$, and X is a positive integer.

5. The fibers and filaments of claim 4 wherein the proportion of A polymers and B polymers are approximately equal.

6. Shaped articles formed from a mixture of the polymer (B)

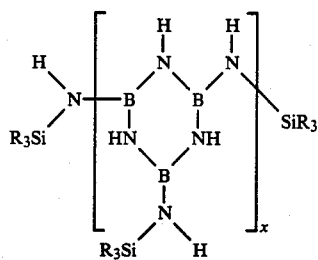

and one or both of the polymers

A'

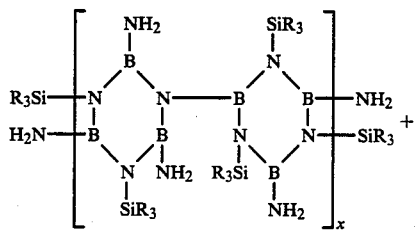

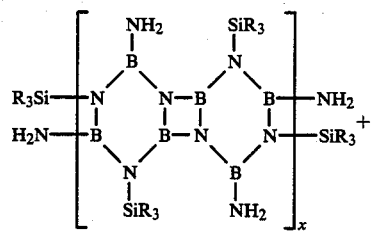

wherein R is lower alkyl of the general formula $C_nH_{2n+1}$, and X is a positive integer.

7. The shaped article of claim 6 wherein A polymers and B polymers are present in approximately equal proportions.

8. The process of preparing the polymer

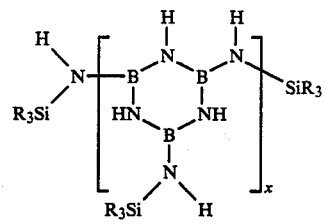

comprising the steps of:
(a) reacting chloroborazine with a disilazine in a mixture of organic solvents, said mixture having at least one aromatic component and at least one non-polar aliphatic component, in an atmosphere of an inert gas, and at a temperature below 0° C. but above the freezing point of said mixture for a period long enough to form a polymer solution;
(b) removing precipitate from said polymer solution; and
(c) then isolating the polymer by removing said solvents from said polymer solution.

9. The process of claim 8, wherein said atmosphere comprises a gas or a mixture of gases selected from nitrogen, helium, and argon.

10. The process of claim 9, wherein said gas or said mixture of gases is at ambient pressure.

11. The process of claim 8, wherein chloroborazine and hexamethyldisilazane are reacted in a solvent mixture comprising equal parts of benzene and hexane for a period of from about 3 to about 24 hours at temperatures from about −50° to −30° C.

* * * * *